(12) United States Patent
Tockman et al.

(10) Patent No.: US 7,935,075 B2
(45) Date of Patent: May 3, 2011

(54) SELF-DEPLOYING VASCULAR OCCLUSION DEVICE

(75) Inventors: Bruce A. Tockman, Scandia, MN (US); Scott A Stockmoe, Maple Grove, MN (US); Eric T. Johnson, Temecula, CA (US); John S. Greenland, San Diego, CA (US); Gary L. Hague, Carlsbad, CA (US); William E. Webler, Escondido, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1008 days.

(21) Appl. No.: 11/115,594

(22) Filed: Apr. 26, 2005

(65) Prior Publication Data

US 2006/0241735 A1    Oct. 26, 2006

(51) Int. Cl.
*A61M 1/00*    (2006.01)
(52) U.S. Cl. ............. 604/34; 604/101.02; 604/103.01; 604/103.12; 604/508; 604/509; 604/510; 600/31; 600/109; 606/34
(58) Field of Classification Search ............ 604/34, 604/101.02, 103.01, 103.12, 508–510; 600/31, 600/109; 606/34
See application file for complete search history.

(56) References Cited

U.S. PATENT DOCUMENTS

| | | | |
|---|---|---|---|
| 3,592,183 A * | 7/1971 | Watkins et al. ............. 600/18 |
| 4,407,271 A * | 10/1983 | Schiff ........................ 600/17 |
| 5,011,488 A * | 4/1991 | Ginsburg .................... 606/159 |
| 5,775,327 A | 7/1998 | Randolph et al. |
| 5,792,094 A * | 8/1998 | Stevens et al. .............. 604/4.01 |
| 5,795,325 A * | 8/1998 | Valley et al. ................ 604/509 |
| 5,800,457 A * | 9/1998 | Gelbfish .................... 606/200 |
| 5,882,329 A * | 3/1999 | Patterson et al. ............ 604/500 |
| 5,916,193 A * | 6/1999 | Stevens et al. .............. 604/509 |
| 5,989,281 A * | 11/1999 | Barbut et al. ............... 606/200 |
| 6,001,118 A * | 12/1999 | Daniel et al. ............... 606/200 |
| 6,007,557 A * | 12/1999 | Ambrisco et al. ........... 606/200 |
| 6,010,522 A * | 1/2000 | Barbut et al. ............... 606/200 |
| 6,014,589 A * | 1/2000 | Farley et al. ................ 607/98 |
| 6,090,097 A * | 7/2000 | Barbut et al. ............... 604/511 |
| 6,113,584 A | 9/2000 | Morley et al. |
| 6,231,544 B1 * | 5/2001 | Tsugita et al. .............. 604/104 |
| 6,245,087 B1 * | 6/2001 | Addis ....................... 606/200 |
| 6,319,242 B1 * | 11/2001 | Patterson et al. ............ 604/508 |
| 6,368,338 B1 * | 4/2002 | Konya et al. ............... 606/200 |
| 6,406,471 B1 * | 6/2002 | Jang et al. .................. 604/540 |
| 6,423,089 B1 * | 7/2002 | Gingras et al. .............. 623/1.11 |
| 6,447,505 B2 * | 9/2002 | McGovern et al. .......... 606/41 |
| 6,485,456 B1 * | 11/2002 | Kletschka ................... 604/96.01 |
| 6,575,933 B1 * | 6/2003 | Wittenberger et al. ...... 604/101.02 |
| 6,589,208 B2 * | 7/2003 | Ewers et al. ............... 604/104 |
| 6,638,294 B1 * | 10/2003 | Palmer ...................... 606/200 |
| 6,652,555 B1 * | 11/2003 | VanTassel et al. ........... 606/200 |
| 6,689,150 B1 * | 2/2004 | VanTassel et al. ........... 606/200 |
| 6,709,415 B2 | 3/2004 | Navia et al. |
| 6,723,085 B2 * | 4/2004 | Jang et al. .................. 604/540 |
| 6,743,196 B2 * | 6/2004 | Barbut et al. ............... 604/101.01 |
| 6,767,345 B2 * | 7/2004 | St. Germain et al. ........ 604/507 |

(Continued)

*Primary Examiner* — Nicholas D Lucchesi
*Assistant Examiner* — Scott Medway
(74) *Attorney, Agent, or Firm* — Faegre & Benson LLP (57) ABSTRACT

The present invention provides a cardiac vascular occlusion system which includes inner and outer guide catheters and an occluding member disposed on the inner catheter. The occluding member may be deployed from a compressed to an expanded position to limit retrograde blood flow in a body lumen. The occluding member may be used when injecting a contrast agent into the body lumen.

9 Claims, 10 Drawing Sheets

U.S. PATENT DOCUMENTS

| | | | |
|---|---|---|---|
| 6,949,122 B2 * | 9/2005 | Adams et al. | 623/2.36 |
| 7,066,904 B2 * | 6/2006 | Rosenthal et al. | 604/103.08 |
| 7,232,452 B2 * | 6/2007 | Adams et al. | 606/200 |
| 7,374,560 B2 * | 5/2008 | Ressemann et al. | 604/509 |
| 7,585,309 B2 * | 9/2009 | Larson | 606/200 |
| 7,713,282 B2 * | 5/2010 | Frazier et al. | 606/200 |
| 2001/0056273 A1 * | 12/2001 | Ewers | 604/509 |
| 2002/0072730 A1 * | 6/2002 | McGill et al. | 604/525 |
| 2002/0161394 A1 * | 10/2002 | Macoviak et al. | 606/200 |
| 2002/0177835 A1 * | 11/2002 | Zadini et al. | 604/385.12 |
| 2004/0172004 A1 | 9/2004 | Mohl | |
| 2005/0015048 A1 | 1/2005 | Chiu et al. | |
| 2005/0043678 A1 * | 2/2005 | Freyman et al. | 604/103.01 |
| 2005/0101902 A1 | 5/2005 | Navia et al. | |
| 2006/0173490 A1 * | 8/2006 | Lafontaine et al. | 606/200 |
| 2006/0175490 A1 * | 8/2006 | Ware et al. | 248/218.4 |
| 2006/0241735 A1 * | 10/2006 | Tockman et al. | 607/122 |

* cited by examiner

Fig. 7B

SELF-DEPLOYING VASCULAR OCCLUSION DEVICE

TECHNICAL FIELD

The present invention relates to an occlusion device for occluding or restricting the flow of blood in a vessel, and in particular to an occlusion device that self-deploys when subjected to blood flow in a vessel of a patient's vascular system.

BACKGROUND

Cardiac function management systems are used to treat arrhythmias and other abnormal heart conditions. Such systems generally include cardiac leads, which are implanted in or about the heart, for delivering an electrical pulse to the cardiac muscle, for sensing electrical signals produced in the cardiac muscle, or for both delivering and sensing.

During the cardiac lead placement procedure, it often becomes necessary and/or desirable to inject a contrast agent in the vicinity of the coronary sinus and then to form an image of the coronary sinus and surrounding vasculature in order to identify an appropriate vessel for lead placement. For example, a physician may perform a venogram procedure in which a radiopaque contrast agent is injected in the vicinity of the cardiac sinus, and then an X-ray image of the cardiac sinus is then taken. One difficulty physicians face when injecting a contrast agent in this manner is that retrograde blood flow tends to prematurely disperse the contrast agent such that the images of the desired blood vessels lack sufficient clarity for a physician to sub-select an appropriate vessel for lead placement. This contrast agent dispersion problem is particularly noticeable in the coronary sinus, which has a relatively large diameter and consequently passes a relatively high volume of blood.

Physicians face similar difficulties when injecting substantially transparent fluids (e.g., saline or dextrose) prior to light or ultrasound imaging of the vessel, and/or prior to subjecting a vessel to photodynamic and/or RF/electrical therapy. Such transparent fluids are used to provide an improved pathway or window for energy exposure, but may be carried away prematurely by blood flow. Further difficulties are faced by physicians injecting therapeutic agents for intravascular treatment of a condition. Typically, the therapeutic agent should be maintained in a specific location or region for at least a minimum time period. However, blood flow tends to carry the therapeutic agent away from the desired site prematurely.

There is a need in the art for a device adapted to occlude blood flow in a vessel to help maintain an injected substance at a target site in the vessel. There is a further need for a device which deploys readily and reliably.

SUMMARY

The present invention, according to one embodiment, is a cardiac lead implantation system. The system includes an outer catheter having a proximal end and a distal end and an outer tubular wall which defines an outer lumen extending between the proximal and distal ends and an inner catheter having a proximal end and a distal end and an inner tubular wall which defines an inner lumen extending between the proximal and distal ends, the inner catheter being sized and shaped to pass through the outer lumen. A self-deploying occluding member is secured to the inner tubular wall. The occluding member is adapted to self-deploy from a compressed position when disposed within the outer lumen to an expanded position when positioned beyond the distal end of the outer catheter. The system further includes a cardiac lead for implantation in a coronary vessel, the cardiac lead being adapted to extend through either the inner or the outer lumen.

According to another embodiment, the present invention is a method for delivering contrast agent to a coronary vessel in a patient. The method includes guiding an outer catheter into the vicinity of the coronary vessel, the outer catheter having a proximal end and a distal end and including an outer tubular wall defining an outer lumen extending between the proximal and distal ends. It further includes guiding an inner catheter through the outer lumen and past the distal end of the outer catheter, the inner catheter having a proximal end and a distal end, and including an inner tubular wall defining an inner lumen extending between the proximal and distal ends, wherein the inner catheter further includes an occluding member secured to the inner tubular wall, the occluding member being retained in a compressed position when disposed within the outer lumen. The occluding member is deployed to an expanded position by moving either the inner catheter or the outer catheter longitudinally such that the occluding member is moved beyond the distal end of the outer catheter and into the expanded position to restrict retrograde blood flow. A contrast agent is delivered to the coronary vessel while the occluding member is in the expanded position.

Another embodiment of the present invention is a device for occluding a blood vessel. The device includes a guide having proximal and distal ends and defining at least one lumen adapted to deliver a substance to the blood vessel, an occluding member including a frame coupled to the guide and a membrane attached to the frame, wherein the occluding member is adapted to actuate from a compressed position to an expanded position at least partially in response to blood flow in the blood vessel, and a tendon coupled to the guide and extending from the proximal end to near the distal end, the tendon having a tendon distal end coupled to the frame and adapted to at least partially actuate the occluding member.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
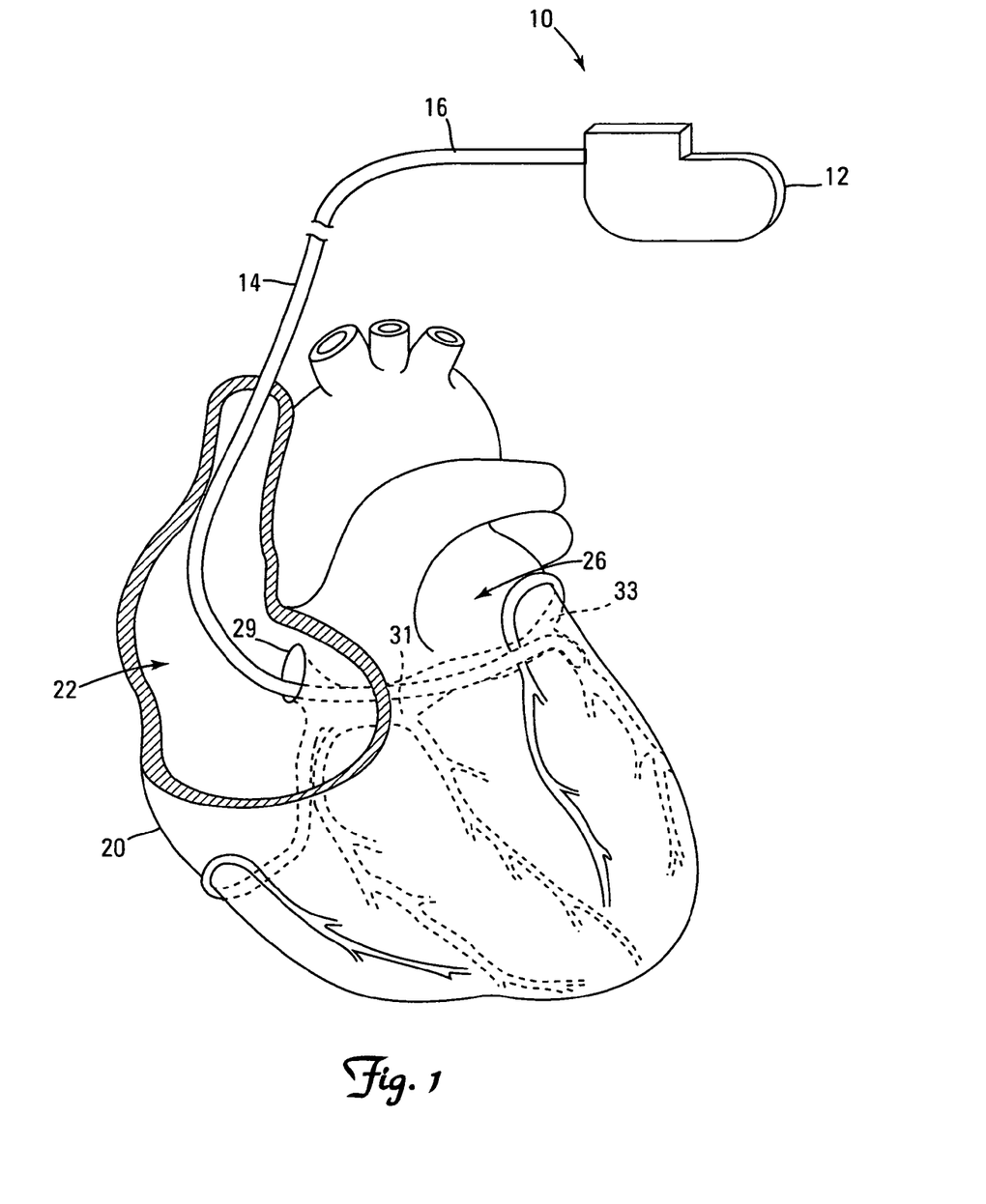
FIG. 1 shows a cardiac lead implanted in the vicinity of a patient's coronary sinus.

FIG. 1 is a schematic drawing of a cardiac rhythm management system 10 including a pulse generator 12 coupled to an lead 14 having a proximal end 16 and a distal end 18. Distal portions of the lead 14 are disposed in the patient's heart 20, which includes a right atrium 22, a right ventricle 24, a left atrium 26, and a left ventricle 28. In the embodiment illustrated in FIG. 1, the distal end 18 of the lead 14 is transvenously guided through the right atrium 22, through the coronary sinus ostium 29, and into a branch of the coronary sinus 31 or great cardiac vein 33. The illustrated position of the lead 14 may be used for sensing, delivering pacing, and/or defibrillation energy to the left side of the heart 20, for the treatment of arrhythmias or other cardiac disorders requiring therapy delivered to the left side of the heart 20.

Figure 2A:
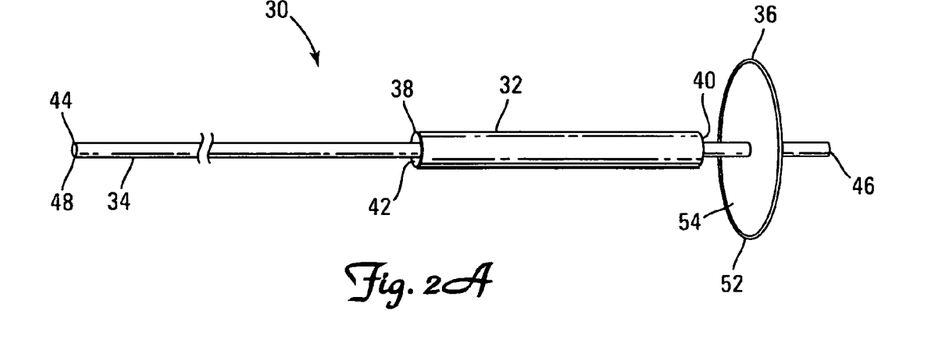
FIGS. 2A-2C show a cardiac vascular occlusion system according to certain embodiments of the present invention.
Figure 2B:
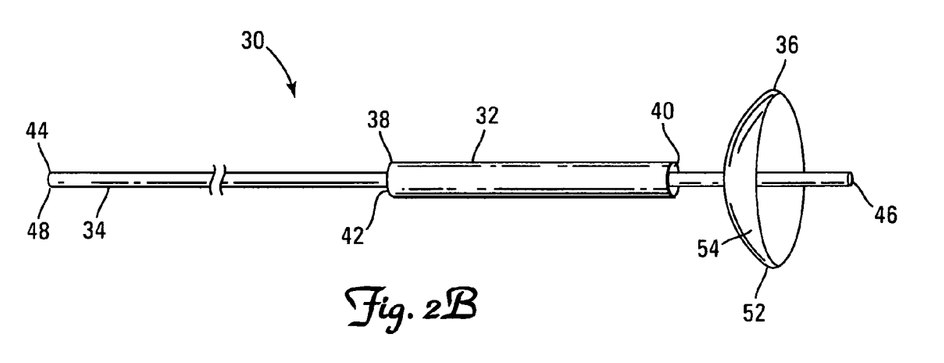
Figure 2C:
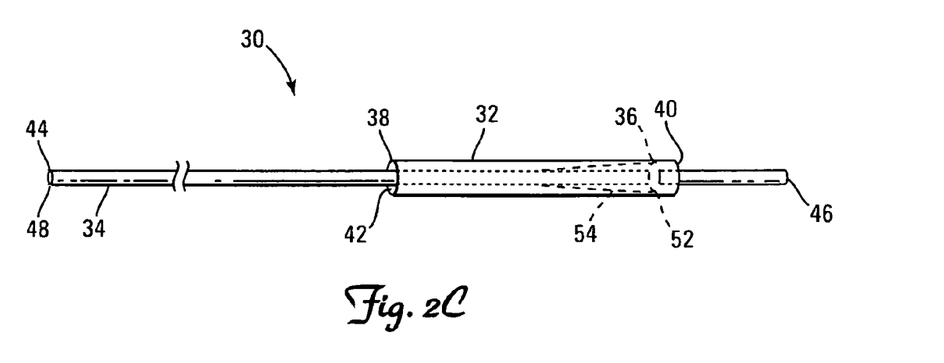

FIGS. 2A-2C show a vascular occlusion system 30 according to various embodiments of the present invention. The vascular occlusion system 30 includes an outer catheter 32, an inner catheter 34, and an occluding member 36. The outer catheter has a proximal end 38, a distal end 40, and a lumen 42 extending between the proximal end 38 and the distal end 40. The inner catheter 34 also has a proximal end 44, a distal end 46 and a lumen 48 extending between the proximal and distal ends 44, 46. The inner catheter 34 is sized and shaped to slide within the lumen 42 of the outer catheter 32. According to one embodiment, the inner catheter 34 is a guidewire, which may or may not include an internal lumen.

The occluding member 36 is shown in an expanded position in FIGS. 2A-2B, and in a compressed position within the lumen 42 of the outer catheter 32 in FIG. 2C. The occluding member 36 is attached to the inner catheter 34 and includes a frame portion 52 and a membrane portion 54. The frame portion 52 is configured to allow expansion from the compressed position (FIG. 2C) to the expanded position (FIGS. 2A-2B) upon being deployed from the outer catheter 32. The frame portion 52 may be formed in a variety of shapes and from a variety of conventional materials, including stainless steel, nitinol, and nickel/titanium alloys, as well as various shape memory alloys and polymers.

The membrane portion 54 is attached to the frame portion 52 and is configured to unfold, inflate, or expand upon deployment from the outer catheter 32 depending on the material used to form the frame portion 52 and the membrane portion 54. In one embodiment, the membrane portion 54 may be formed from a relatively resilient material, including without limitation a variety of conventional polymeric materials as well as the materials used to form the frame portion 52, such that the membrane portion 54 tends to block and/or re-circulate blood. For example, the relatively flat occluding member 36 shown in FIG. 2A may tend to block fluid flow. In contrast, the concave shape shown in FIG. 2B may tend to redirect and/or re-circulate blood flow in the opposite direction, thereby creating flow turbulences and/or eddies to impede normal blood flow.

In another embodiment, the membrane portion 54 may be formed from a more elastic polymer such that the membrane portion 54 tends to occlude by inflating. Suitable materials for the membrane portion 54 generally include substantially fluid impermeable materials such as silicone, polyurethane, and other biocompatible thermoplastic polymers. The membrane portion 54 may also be semi-permeable. In one embodiment, the occluding member 36 may be formed from a unitary piece of material.

In one embodiment, the occluding member 36 self-expands after deployment from the outer catheter 32. Alternatively, the occluding member 36 could be manually deployed through the use of strings, tendons, wires, or other members attached to the occluding member 36 and extending to the proximal ends of the outer and inner catheters 32, 34. Alternatively or additionally, the occluding member 36 could expand by inflating when exposed to fluid (e.g., blood) flow.

Figure 3A:
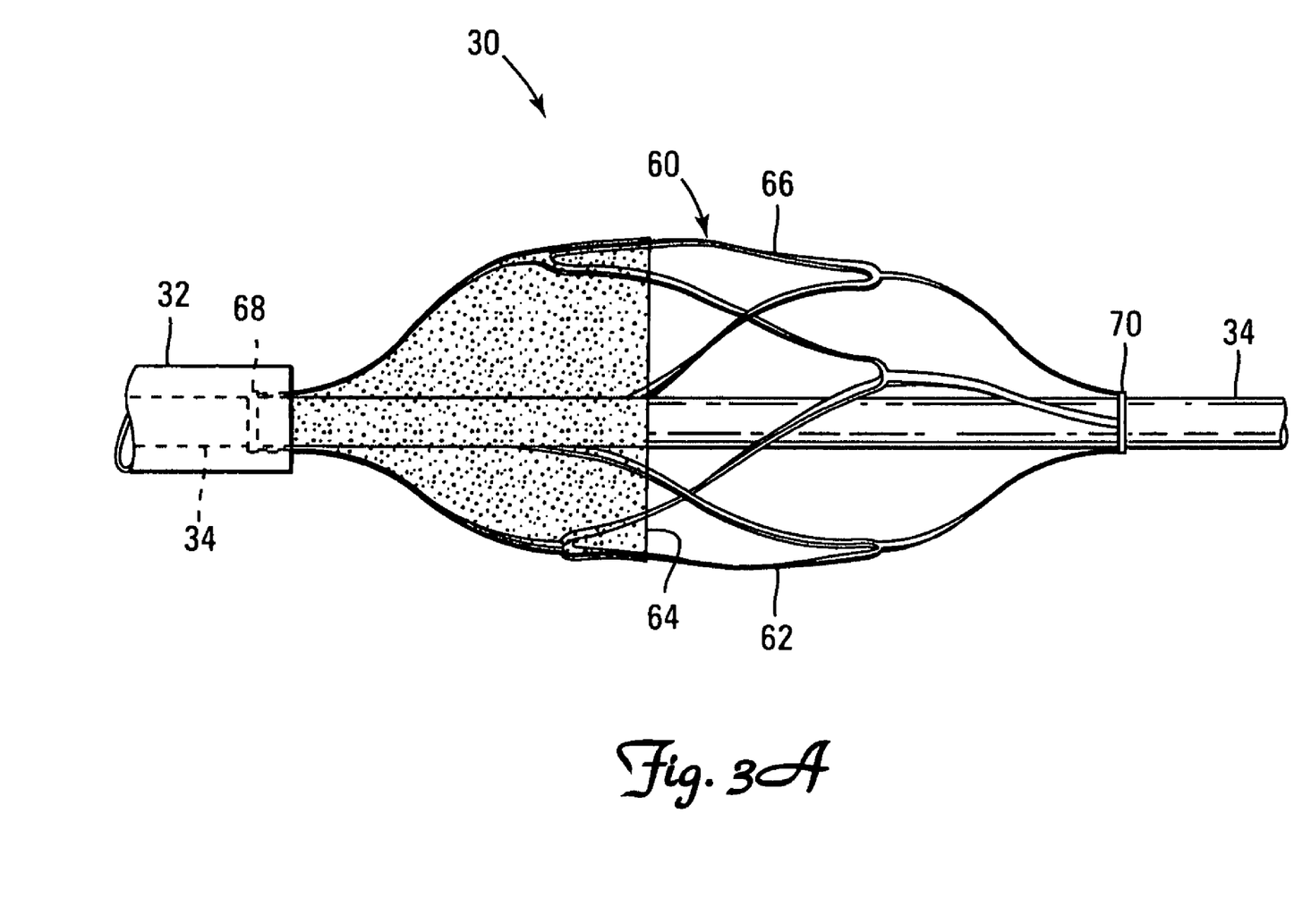
FIGS. 3A-3B show a cardiac vascular occlusion system according to another embodiment of the present invention.
Figure 3B:
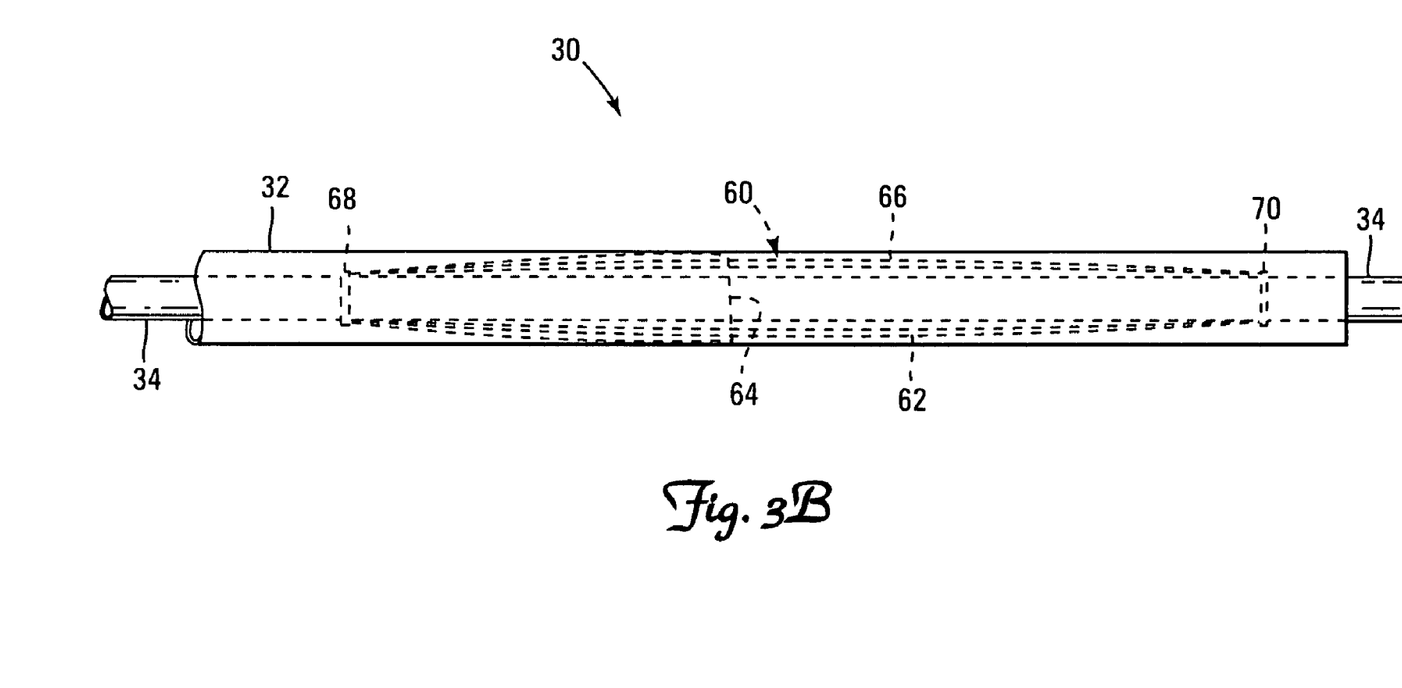

FIGS. 3A-3B show perspective views of a vascular occlusion system 30 according to another embodiment of the present invention. FIG. 3A shows the system 30 in an expanded configuration, and FIG. 3B shows the system 30 in a compressed configuration. As shown in FIGS. 3A-3B, the system 30 includes an occluding member 60, which includes a frame 62 and a membrane portion 64. The frame 62 may have a shape and function similar to a conventional stent or embolic protection device, and includes struts 66 connected at each end to rings 68, 70. The frame 62 provides a scaffolding upon which the membrane portion 64 resides.

The frame 62 may be self-expanding such that the occluding device 60 expands upon deploying from the outer catheter 32. Alternatively, the frame 62 may be biased to a compressed position, but may expand in response to the force generated by the flow of fluid in the vessel against the membrane portion 64. In either case, one or both of the rings 68, 70 may slide relative to the inner catheter 34 to facilitate the expansion and/or compression of the struts 66. In a particular embodiment, ring 70 may slide, while ring 68 may remain fixed to the lead body.

Figure 4A:
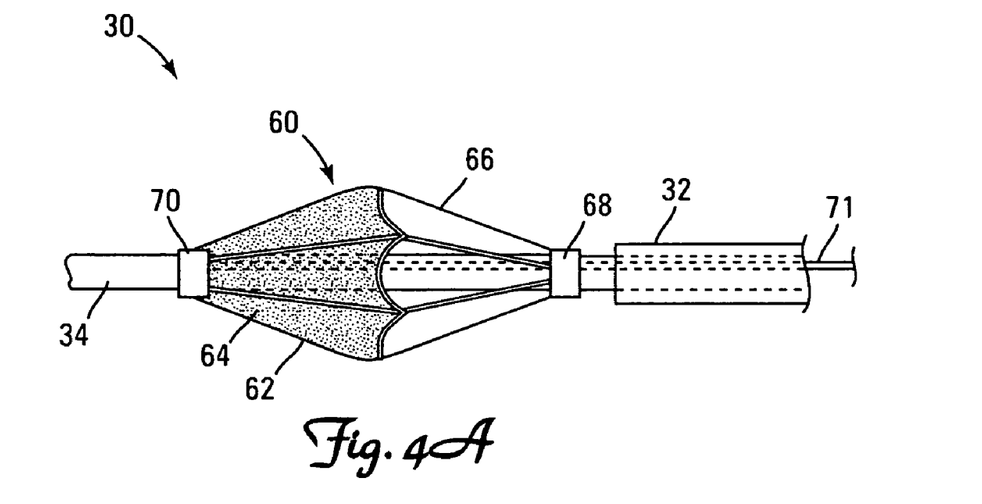
FIGS. 4A-4B show schematic views of a cardiac vascular occlusion system according to another embodiment of the present invention.
Figure 4B:
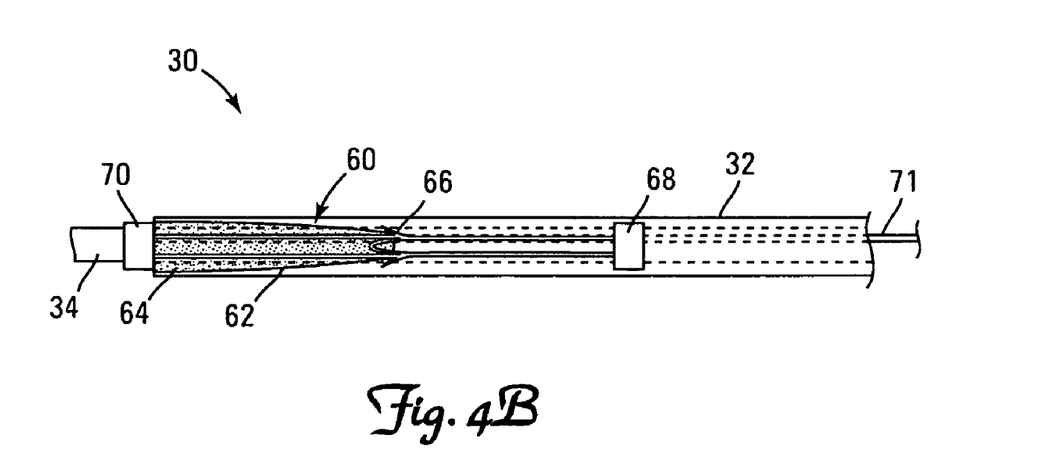

FIGS. 4A-4B show schematic views of a vascular occlusion system 30 according to another embodiment of the present invention. As show in FIGS. 4A-4B, the system 30 includes an outer catheter 32, an inner catheter 34, and an occluding member 60. The occluding member 60, which is coupled to the inner catheter 34, has a frame 62 with rings 68, 70 connected by struts 66 and a membrane portion 64 disposed over a portion of the frame 62. As shown, the membrane portion 64 is disposed on a distal portion of the frame 62 (the left-hand side as shown in FIGS. 4A and 4B), such that the occluding member 60 is configured to occlude blood flowing in the same direction as the insertion path of the vascular occlusion system 30 (e.g., coronary artery applications). According to another embodiment, the membrane portion 64 is disposed on a proximal portion of the frame 62, such that the occluding member 60 is configured to occlude blood flowing in the opposite direction of the insertion path (e.g., coronary vein applications). In one embodiment, the occluding member 60 is held in a collapsed position (see FIG. 4B) by the outer catheter 32 and is deployed by retracting the outer catheter 32 and allowing blood flow to impart a deploying force on the membrane portion 64.

In another embodiment, the vascular occlusion system 30 includes a wire, tendon, or stylet 71 (or similar device), which is adapted to extend through or along the inner catheter 34 and couple to the ring 70. In this embodiment, the ring 70 is configured to slide along the inner catheter 34 to facilitate the expansion (see FIG. 4A) or compression (see FIG. 4B) of the occluding member 60. The stylet 71 may be used to push or pull the ring 70 along the inner catheter 34. In this embodiment, the ring 68 is fixed, such that motion of the ring 70 proximally causes a radial expansion of the struts 66, which in turn causes an expansion or opening of the membrane portion 64. Once the membrane portion 64 opens slightly, blood flow in the vessel will impart a force on the membrane portion 64 causing full deployment.

In one embodiment, the ring 70 is fixed with respect to the inner catheter 34 and the stylet 71 is coupled to the ring 68, which may slide distally to cause a radial expansion of the struts 66. In one embodiment, the inner catheter 34 includes a port or opening, which is disposed between the locations of the rings 68, 70 while the occluding member 60 is in the expanded position (see FIG. 4A). This opening may be used to inject a contrast agent or other substance through a lumen of the inner catheter 34 to within the occluded vessel. The stylet 71 may be located in the same lumen of the catheter 34 that is used to inject a contrast agent or other substance, or it may be located in a separate lumen. In one embodiment, the catheter 34 includes two or more coaxial lumens, and the stylet 71 is located in an outer lumen located, for example, between two layers of the catheter 34.

In one embodiment, the vascular occlusion system 30 does not include the outer catheter 32, but instead includes only a single guide or catheter 34. In this embodiment, the tendon or stylet 71 is operable to cause axial movement of one of the rings 68, 70, with respect to the other. In this embodiment, the occluding member 60 can be deployed by applying a force to the stylet 71 to cause one of the rings 68, 70 to move toward the other, which causes a radial expansion of the struts 66. In another embodiment, occluding member 60 does not include the rings 68, 70. In this embodiment, the stylet 71 is coupled to a portion of the frame 62 and the occluding member 60 is deployed by using the stylet 71 to effect an axial compression and corresponding radial expansion of the frame 62.

This radial expansion of the struts 66 causes an opening of the membrane portion 64. Blood flow in the vessel then impacts the membrane portion 64 and causes full deployment. This deployment of the membrane portion 64 causes at least a partial occlusion of blood flow in the vessel. A contrast agent (or other substance) can then be injected into the vessel through a lumen of the catheter 34. The occluding member 60 can be collapsed by using the stylet 71 to expand the distance between the rings 68, 70, which in turn causes the struts 66 and thus the membrane portion 64 to move adjacent the catheter 34. In one embodiment, the frame 62 is predisposed to hold the membrane portion 64 against the catheter 34.

Figure 5A:
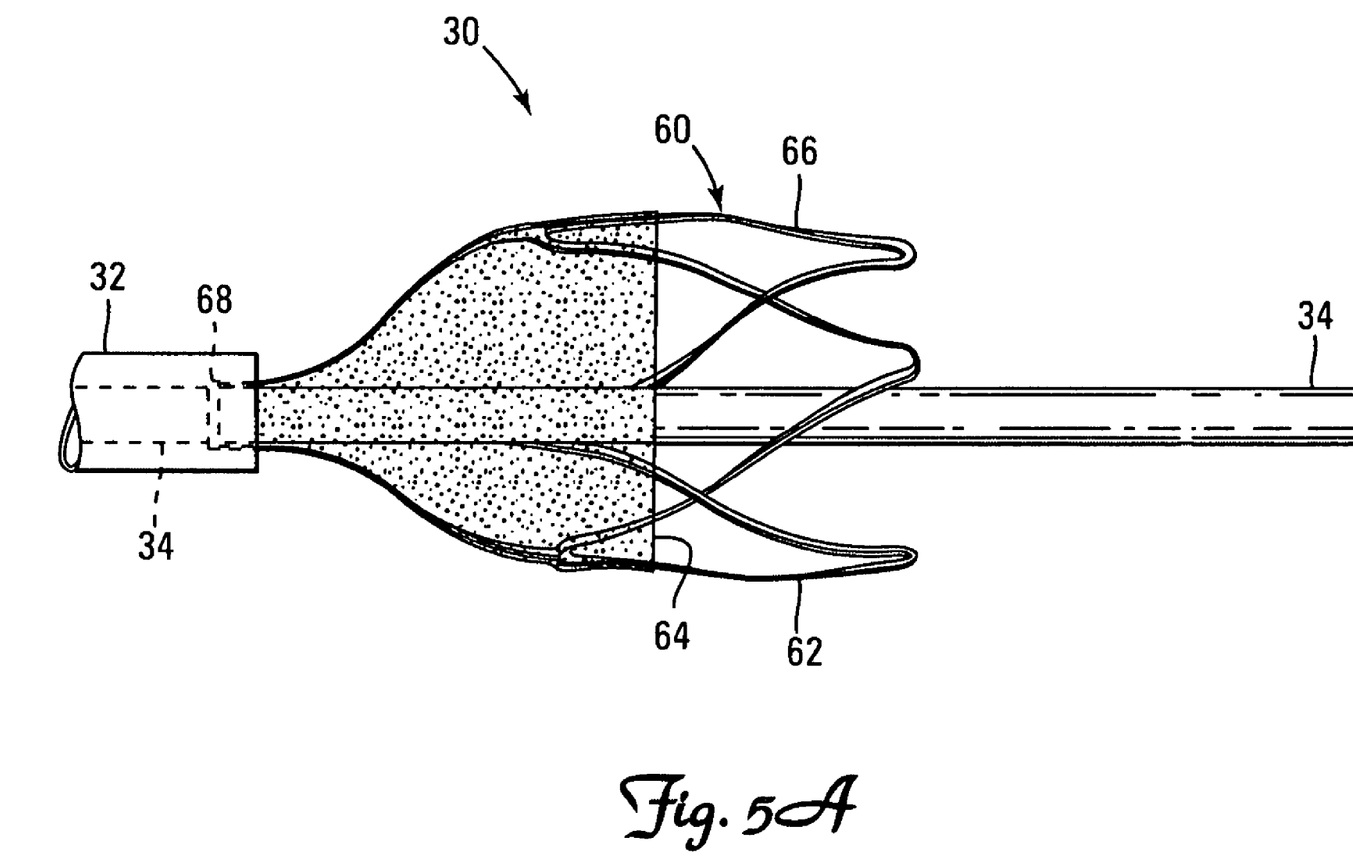
FIGS. 5A-5B show a cardiac vascular occlusion system according to another embodiment of the present invention.
Figure 5B:
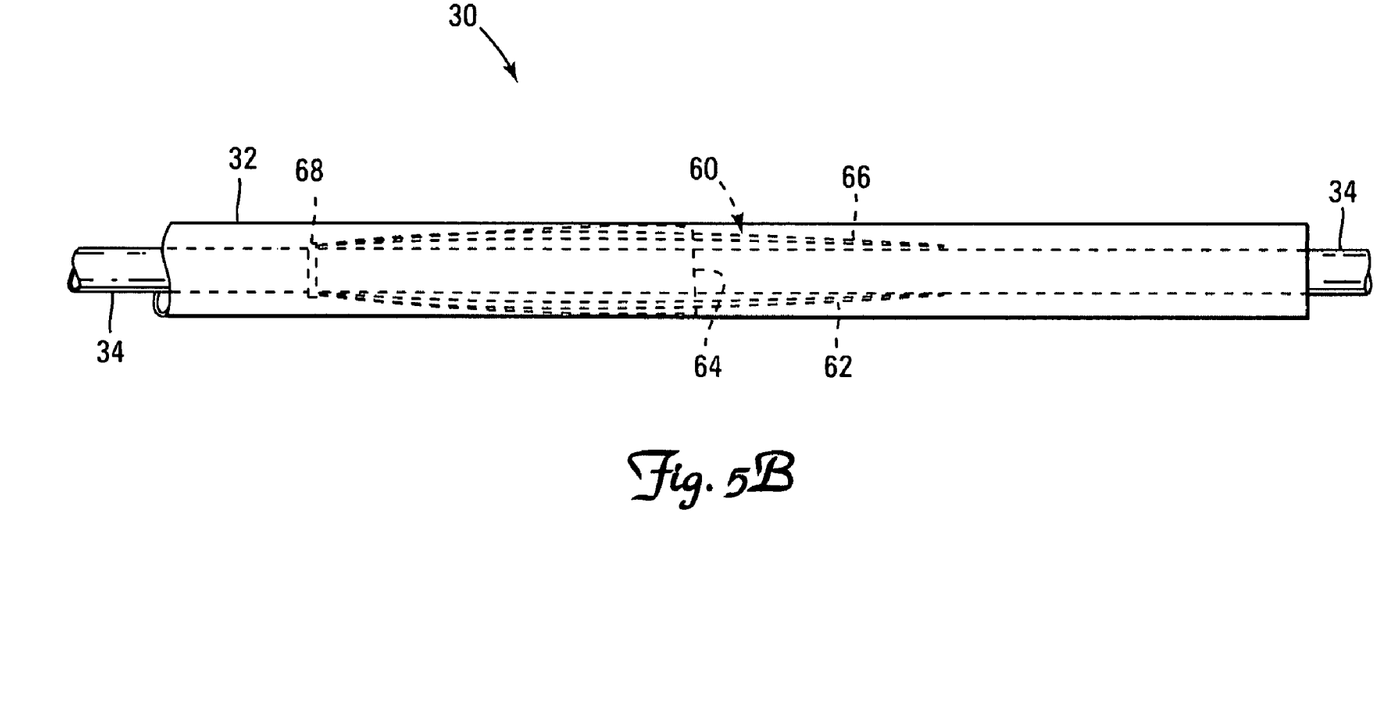

FIGS. 5A-5B show perspective views of a vascular occlusion system 30 according to another embodiment of the present invention. As shown in FIGS. 5A-5B, the frame 62 again includes a plurality of struts 66 which form a stent-like shape. In this embodiment, as compared to that of FIGS. 3A-3B, the distal end of the frame 62 is not crimped down or secured to the inner catheter 34 when expanded. The proximal end of the frame 62 is attached to the inner catheter 34, for example, by a ring 68, which may be movable or remain fixed relative to the inner catheter 34. In either case, the frame self-expands, or expands under the force generated by blood flow against the membrane 64, to occlude the desired vessel, and may be compressed by sliding outer catheter 32 distally over the occluding member 60.

The occluding member 36 or 60 may also be adjustable along various positions on the inner catheter 34. In one embodiment, the occluding member 36 or 60 is disposed proximally to the distal end of the inner catheter 34. For example, the occluding member 36 or 60 may be positioned between about 2 cm and about 5 cm from the distal end of the inner catheter 34. One benefit of setting the occluding member 36 or 60 back from the distal end of the inner catheter 34 is that when a contrast agent is injected while the occluding member 36 or 60 is expanded, it may take longer for the contrast agent to flow past the occluding member 36 or 60.

In the expanded configuration, the occluding member 36 or 60 may either partially or fully occlude the vessel depending on the diameter of the vessel as compared to the diameter of the occluding member 36 or 60. In embodiments in which only partial occlusion occurs, some blood flow may continue past the occluding member 36 or 60 and through the vessel. Likewise, injected contrast agent may flow past the occluding member 36 or 60 such that vessels disposed proximally of the occluding member 36 or 60 may be imaged. One potential benefit of utilizing a self-expanding or flow-expanding occluding member 36 or 60 is that the risk of injuring, perforating, and/or bursting a vessel when the occluding member 36 or 60 expands is minimized as compared to a balloon-type member, which may run the risk of being overfilled during use.

Figure 6:
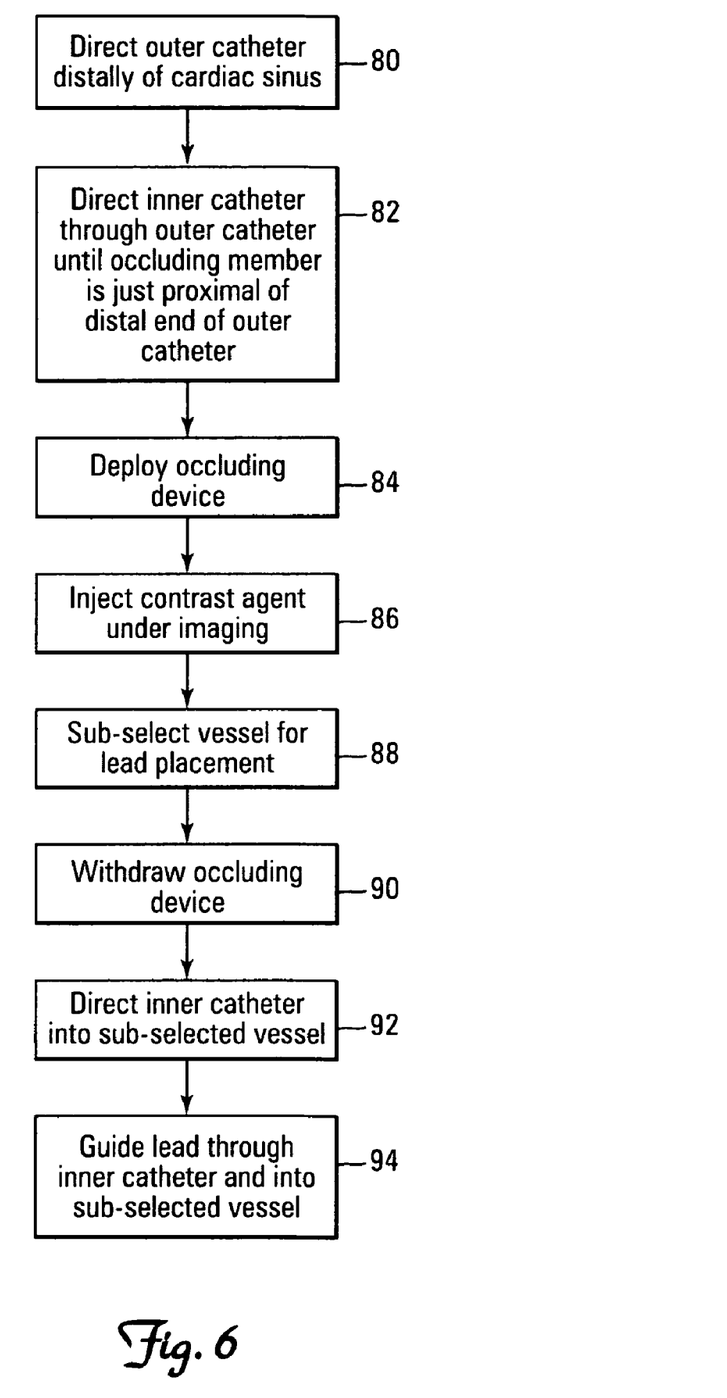
FIG. 6 is a flowchart showing a method of using the cardiac vascular occlusion system according to one embodiment of the present invention.
Figure 7A:
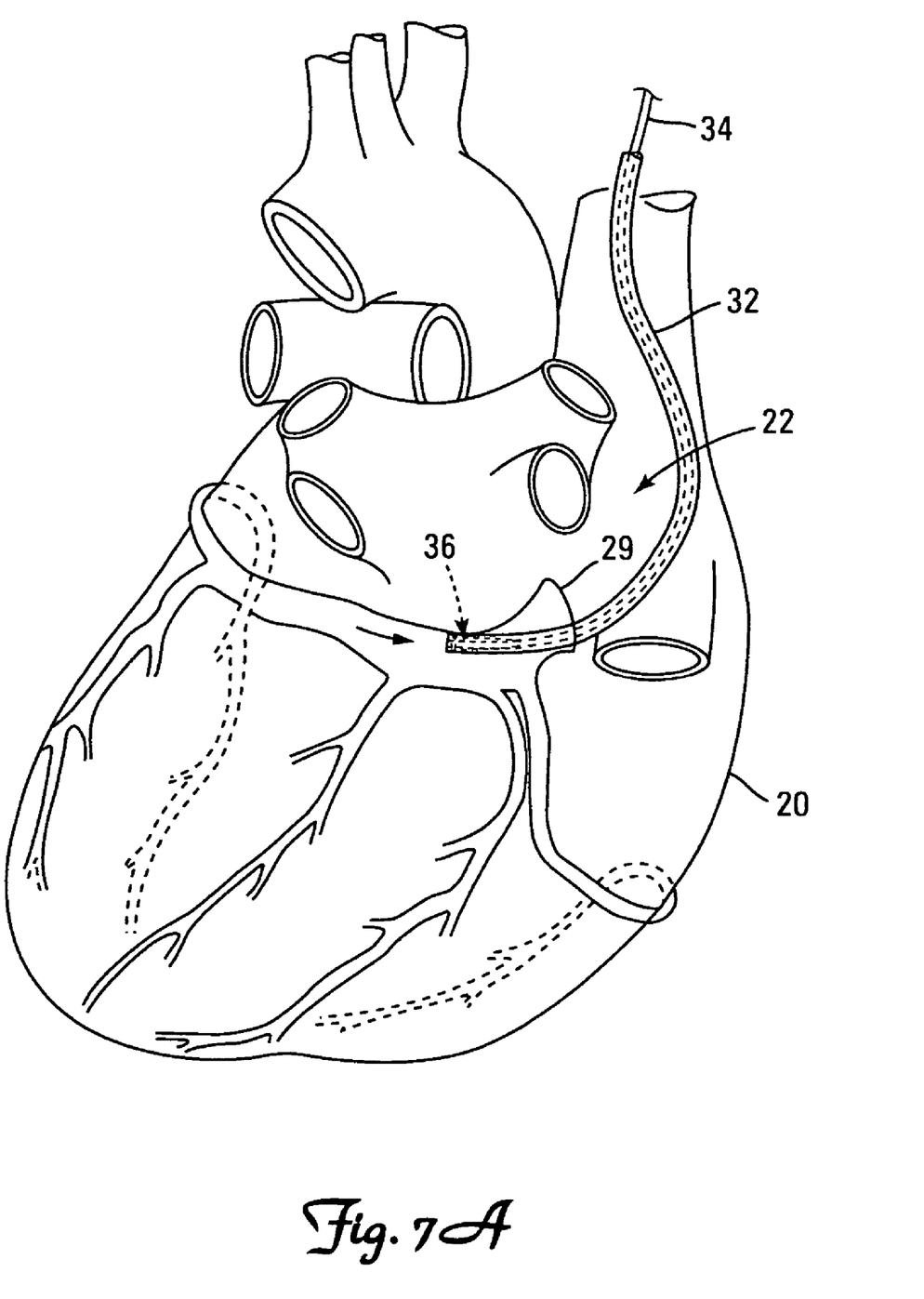
FIGS. 7A-7B shows a cardiac placement system according to one embodiment of the present invention implanted in the vicinity of a patient's coronary sinus.
Figure 7B:
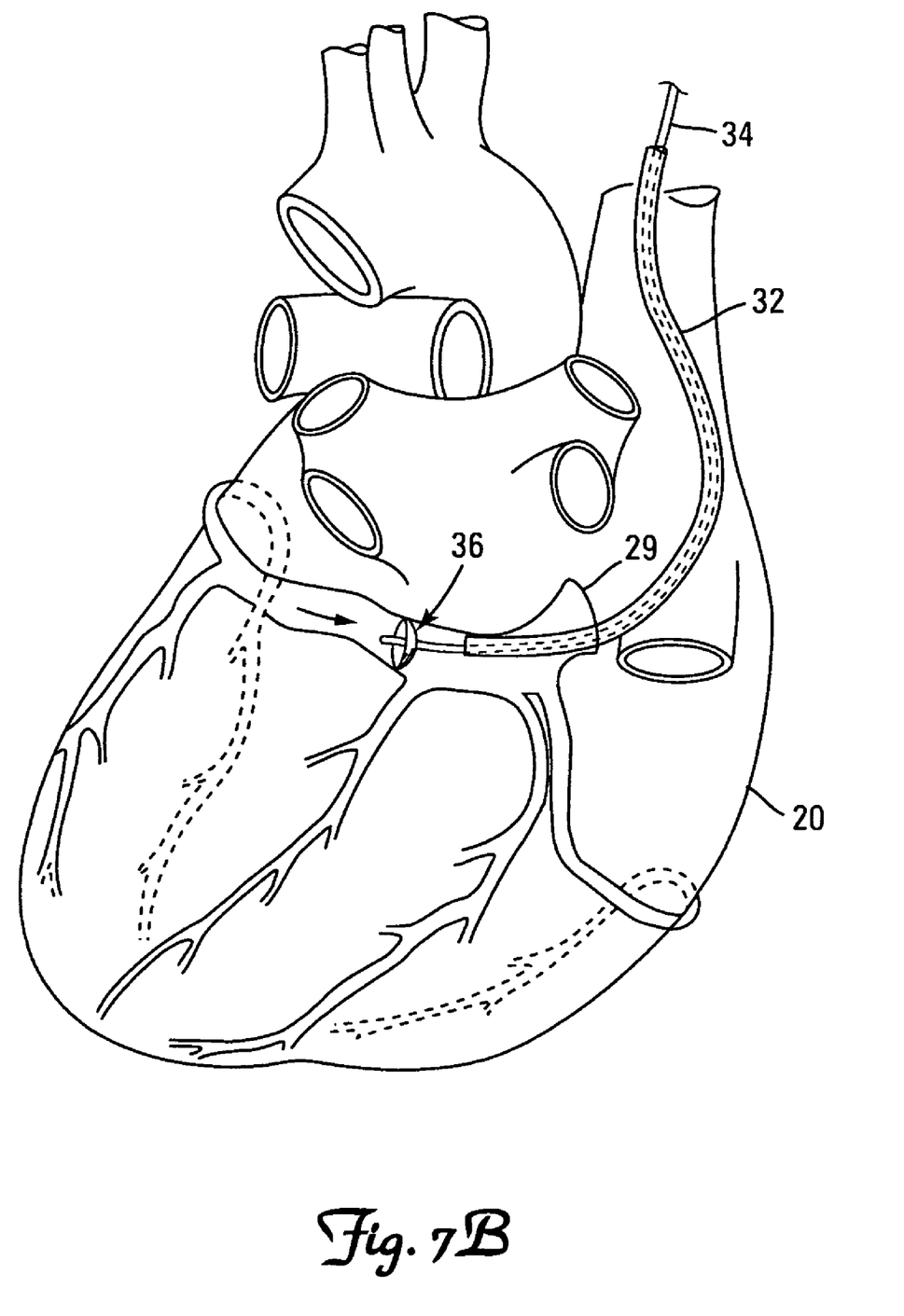

FIG. 6 is a flowchart showing a method of using the vascular occlusion system 30 shown in FIG. 2 according to one embodiment of the present invention. As show, the outer catheter 32 is first directed into a patient's superior vena cava and through the opening of the coronary sinus 29 (block 80). The inner catheter 34 is then guided through the outer catheter 32 until the occluding member 36 is positioned just proximally of the distal end of the outer catheter 32 (block 82) as shown in FIG. 7A. when a clinician decides to image the coronary sinus 29 and surrounding vessels, the occluding member 36 is deployed distally out of the outer catheter 32 by relative movement between the outer catheter 32 and the inner catheter 34 ("84"). The occluding member 36 then expands as shown in FIG. 7B by one of the mechanisms described above in reference to specific embodiments of the present invention.

Upon expansion, the occluding member 36 limits retrograde blood flow (in the direction of the illustrated arrow) out of the coronary sinus. In the illustrated embodiment, the occluding member 36 may reflect the blood flow to create counter-currents (e.g. turbulence or eddies), which in turn, limits retrograde blood flow.

In one embodiment, the occluding member does not necessarily completely prohibit fluid flow, but rather permits a limited volume of fluid to flow proximally of the occluding member. This may allow sufficient quantities of contrast agent to flow proximally of the occluding member to image vessels in that area. It may also reduce risks associated with over-pressurization of the coronary sinus. After deploying the occluding member 36, contrast agent may be injected distally of the occluding member 36 through the inner catheter 34 (block 86). As previously noted, the inner catheter 34 may extend several centimeters past the occluding member 36 to increase the dwell time of the contrast agent in the vessel 38.

During and/or after injecting the contrast agent into the vessel 38, a clinician may image the patient's great cardiac vein region using conventional imaging techniques. The clinician may then utilize the resulting images to sub-select a vessel for subsequent vascular occlusion (block 88). The occluding member 36 is then withdrawn back into the outer catheter 32 (or the outer catheter is forwardly over the occluding member 36) and into the compressed position (block 90).

After the inner catheter 34 and/or outer catheter 32 is directed into the sub-selected vessel (block 92), a cardiac lead 14 may be guided through either the inner catheter 32 or outer catheter 34 and implanted in the desired vessel (block 94) as shown in FIG. 1. Alternatively, a guidewire may be placed in the sub-selected vessel and the lead 14 subsequently implanted. At times, it may become necessary or desirable for the clinician to perform a second imaging procedure after sub-selecting a particular vessel to further facilitate vascular occlusion.

Although certain Figures are directed to the use of occluding members to facilitate cardiac vascular occlusion, other applications of such occluding members are also within the scope of the present invention. Generally speaking, the occluding member of various embodiments of the present invention may be suitable for use in conjunction with catheters and/or other percutaneous devices that are placed in vessels (e.g. arteries, veins, arterioles, venules, capillaries) or other portions of the circulatory system in order to occlude blood flow. For example, the occluding member may be positioned on a guidewire, IVUS Catheter, OCT catheter, or a photodynamic catheter to occlude blood flow during the infusion of a substantially transparent fluid (e.g. saline or dextrose), which replaces blood during the application of imaging or therapeutic energy (e.g. light, ultrasound, RF, electrical) to a vessel.

In another example, the occluding member may be utilized in conjunction with a catheter and/or guidewire to increase the residence time of an infused bioactive agent (e.g. cells, cell derivatives, pharmacological agents) in a vessel. An increased residence time may provide extended treatment at the desired location, and/or may localize the treatment at the desired vessel or tissue site.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A cardiac lead implantation system comprising:
    an outer catheter having a proximal end and a distal end and an outer tubular wall which defines an outer lumen extending between the proximal and distal ends,
    an inner catheter having a proximal end and a distal end and an inner tubular wall which defines an inner lumen extending between the proximal and distal ends, the inner catheter being sized and shaped to pass through the outer lumen, the inner lumen being sized and shaped to facilitate passage of a cardiac lead;
    a completely fluid impermeable expandable membrane secured to the inner catheter, the completely fluid impermeable expandable membrane having in an expanded position an open distal end receiving retrograde blood flow and a closed, fluid impermeable proximal end occluding and re-circulating the retrograde blood flow such that contrast agent is delivered distally of the membrane to provide imaging contrast in a region where visualization is desired; and
    a cardiac lead for implantation in a coronary vessel, the cardiac lead being adapted to extend through the inner lumen.

2. The system of claim 1 wherein the membrane is adapted to self-expand upon deployment from the outer lumen.

3. The system of claim 1 wherein the fluid impermeable membrane includes a self-expanding frame secured to the inner tubular wall.

4. The system of claim 3 wherein the frame includes a plurality of struts secured to at least one ring which encircles the inner tubular wall.

5. The system of claim 4 wherein the struts are secured at each end to proximal and distal rings, and wherein at least one of the proximal and distal rings slides relative to the inner tubular wall when the membrane moves between the compressed position and expanded positions.

6. The system of claim 1 wherein the membrane comprises a collar, concave disk, sail, parachute, web or stent-like configuration.

7. The system of claim 1 wherein the membrane is securable at a plurality of positions along the inner tubular wall.

8. The system of claim 1 further comprising a sheath adapted to slide between inner and outer catheters to deploy the membrane from the distal end of the outer catheter.

9. The system of claim 1 further comprising one or more elongate members attached to the membrane to deploy the membrane from the distal end of the outer catheter.

* * * * *